United States Patent
Gao

(10) Patent No.: US 6,541,263 B2
(45) Date of Patent: Apr. 1, 2003

(54) DETERMINATION OF CORTICOSTEROIDS IN HUMAN PLASMA USING MICROMASS LC/MS/MS

(75) Inventor: Feng Gao, Stamford, CT (US)

(73) Assignee: Euro-Celtique, S.A. Luxembourg (LU)

( * ) Notice: Subject to any disclaimer, the term of this patent is extended or adjusted under 35 U.S.C. 154(b) by 24 days.

(21) Appl. No.: 09/788,353

(22) Filed: Feb. 21, 2001

(65) Prior Publication Data

US 2002/0168775 A1 Nov. 14, 2002

(51) Int. Cl.$^7$ .............................................. G01N 33/92
(52) U.S. Cl. ........................ 436/71; 436/101; 436/173; 436/139
(58) Field of Search ......................... 436/71, 161, 173, 436/139

(56) References Cited

U.S. PATENT DOCUMENTS

| | | | |
|---|---|---|---|
| 5,922,340 A | 7/1999 | Berde et al. | 424/426 |
| 5,990,284 A | 11/1999 | Mahiou et al. | 530/376 |
| 6,071,910 A | 6/2000 | Gleich et al. | 514/235.5 |

OTHER PUBLICATIONS

Bagnati et al. (Anal. Biochem.) disclose an analysis of dexamethasone and betamethasone in bovine urine by purification with an "on–line" immunoaffinity chromatography—HPLC system . . . , Anal. Biochem., v. 235, 119–126.*
Creaser et al., "Immunoaffinity chromatography combined online with the high–performance liquid chromatography–mass spectrometry for the determination of corticosteroids" J. Chromat., A (1998), 794(1+2), 37–43.*

Fiori et al. "Identification of main corticosteroids as illegal feed additives in milk replacers by liquid chromatography–atmospheric pressure chemical ionization mass spectrometry", J. Chromat., A (1998), 807(2), 219–227.*
Fredline et al., "A reference method for the analysis of aldosterone in blood by high–performance liquid chromatography–atmospheric pressure chemical ionization–tandem mass spectrometry", Anal. Biochem. (1997), 252(2), 308–313.*
Yoshitake et al. "Measurement of 21–hydroxy corticosteroids in human and rat sera by high performance liquid chromatography with flourometric detection", J. Chromatogr., 1989, v. 489 (2), pp. 364–70 (Abstract).*
Guo et al., "Identification of nine corticosteroids with high–performance liquid chromatography–mass spectrometry", Yaoxue Xuebao (1999), 34(12), 928–932 (Abstract).*
Williams et al. "High–Pressure Liquid Chromatographic Determination of Corticosteroids in Topical Pharmaceuticals", J. Pharm. Sci. May 1981, v. 70, No. 5, pp. 530–534.*
Savu et al. "A Confirmatory HPLC–MS/MS Method for Ten Synthetic Corticosteroids in Bovine Urines", J. Mass. Spectrom., 1966, v. 31, pp. 1351–1363.*

(List continued on next page.)

Primary Examiner—Jill Warden
Assistant Examiner—Yelena Gakh
(74) Attorney, Agent, or Firm—Pennie & Edmonds LLP

(57) ABSTRACT

The present invention is directed to a method of detecting a corticosteroid in a sample by adding an internal standard to a sample suspected of containing a corticosteroid; removing interfering compounds from the sample; placing the sample on an HPLC column equilibrated with a $NH_4OAc:MeOH$ solution and collecting an eluent; and analyzing the eluent of the HPLC column with a MS, wherein if contained in the sample, the corticosteroid forms an adduct that is detected by the MS.

8 Claims, 3 Drawing Sheets

OTHER PUBLICATIONS

Honing et al. "Adduct Formation of Steroids in APCl and its Relation to Structure Identification", Analusis, 2000, v. 28, No. 10, pp. 921–924.*

Antignac et al. "Collision–Induced Dissociation of Corticosteroids in Electrospray Tandem Mass Spectrometry and Development of a Screening . . .", Rapid Comm. Mass Spectr., 2000, v. 14, pp. 33–39.*

T. Yoshitake et al., "*Measurement of 21–Hydroxycorticosteroids in Human and Rat Sera by High–Performance Liquid Chromatography with Fluorimetric Detection,*" *J. Chromatrogr.* 489(2):364–70 (1989).

Schmelzer, H.G. et al., *Angewandte Chem. International Edit., 5,* No. 11 (1966) 960–961.

Curley, Joanne et al., *Anesthesiology*, V 84, No. 6, (Jun. 1996) 1401–1410.

Dräger, Christiane et al., Anesthesiology, V 89, No. 4, (Oct. 1998) 969–979.

Gu, Xiao Qing et al., *Journal of Chromatography* B, 719 (1998) 284–290.

Le Guévello, P et al., *Journal of Chromatography*, 622 (1993) 284–290.

Michaelis, Hans Christoph, et al., *Journal of Chromatography*, 527 (1990) 201–207.

Tahrauoi, A et al., *Journal of Pharmaceutical and Biomedical Analysis*, 15 (1996) 251–257.

* cited by examiner

Calibration Curve for Plasma Samples containing Dexamethasone

Calibration Curve for Plasma Samples containing Bupivaciane

Chromatogram of a Plasma Sample known to have Dexamethasone and Bupivacaine

DETERMINATION OF CORTICOSTEROIDS IN HUMAN PLASMA USING MICROMASS LC/MS/MS

1. INTRODUCTION

The invention is directed to methods for quantitatively determining the presence and/or amount of a corticosteroid in a solution by forming a corticosteroid-acetate adduct and detecting the adduct using a micromass LC/MS/MS system. These methods accurately detect trace amounts of corticosteroids. Optionally, these methods further detect other drug agents present in concentrations much greater than the corticosteroids to be detected. Preferably, the methods are used to substantially simultaneously detect and determine the amount of dexamethasone and other compounds such as bupivacaine within human plasma.

2. BACKGROUND OF THE INVENTION

The quick and accurate determination of drugs within human plasma is of paramount importance in many medical applications. Methods that accurately and quickly determine even trace amounts of a drug in the bloodstream are particularly useful. Moreover, these detection methods become of particular importance in the use of high potency drugs because unwanted side effects are produced when safe dosage levels are exceeded. Potent drugs can include, for example, glucocorticoids which can exacerbate neuronal damage due to hypoxia, ischemia, seizure, and hypoglycemia. Consequently, research has focused on developing drug detection and/or quantification methods that concurrently analyze samples such as plasma for a variety of compounds in differing amounts. This research, however, has been hampered because detection readings can be misinterpreted when the drugs to be detected are structurally similar to other compounds within the sample and/or the drugs are present in minute concentrations within the sample.

2.1 Corticosteroids

The effects of corticosteroids are numerous and widespread. Their diverse effects include: alterations in carbohydrate, protein, and lipid metabolism; maintenance of fluid and electrolyte balance; and preservation of normal function of the cardiovascular system, the immune system, the kidney, skeletal muscle, the endocrine system, and the nervous system. In addition, by mechanisms that are still not fully understood, corticosteroids provide the organism with the capacity to combat stressful circumstances such as noxious stimuli and environmental changes. For example, in the absence of the adrenal cortex, survival is made possible only by maintaining an optimal environment, including adequate and regular feedings, ingestion of relatively large amounts of sodium chloride, and maintenance of an appropriate environmental temperature.

The actions of corticosteroids are related in complex ways to those of other hormones. For example, in the absence of lipolytic hormones, cortisol has virtually no effect on the rate of lipolysis by adipocytes. Likewise, in the absence of glucocorticoids, epinephrine and norepinephrine have only minor effects on lipolysis. Administration of a small dose of a glucocorticoid, however, markedly potentiates the lipolytic action of these amines. These effects of corticosteroids that involve concerted actions with other hormonal regulators are termed permissive and most likely reflect steroid-induced changes in protein synthesis that, in turn, modify tissue responsiveness.

Corticosteroids include glucocorticoids and mineralocorticoids, including, but not limited to, aldosterone, beclomethasone, betamethasone, corticosterone, cortisol, cortisone, dexamethasone, fludrocortisone, flumethasone, hydrocortisone, 6α-methylprednisolone, 6β-methylprednisolone, paramethasone, prednisolone, prednisone, prednylidene, 4-pregnene-20,21-diol-3,11-diol, presesterone, testosterone, triamcinolone, among others.

Two categories of toxic effects result from the therapeutic use of corticosteroids: those resulting from withdrawal of steroid therapy and those resulting from continued used of supraphysiological doses. There are several complications associated with steroid withdrawal, including acute adrenal insufficiency, resulting from too rapid withdrawal of corticosteroids after prolonged therapy, where the hypothalamic-pituitary-adrenal (HPA) axis has been suppressed. Besides the consequences that result from the suppression of the HPA axis, there are a number of other complications that result from prolonged therapy with corticosteroids. These include fluid and electrolyte abnormalities, hypertension, hyperglycemia, increased susceptibility to infection, osteoporosis, myopathy, behavioral disturbances, cataracts, growth arrest, and the characteristic habitus of steroid overdose including fat redistribution, striae, ecchymoses, acne, and hirsutism.

Traditionally, detection methods of corticosteroids have been limited by the inability to detect amounts lower than 100 pg/ml, interference by other compounds including other corticosteroids, extensive and tedious sample preparation, derivatization of samples prior to analysis, or a combination these limitations.

2.2 Dexamethasone

Dexamethasone possesses glucocorticoid activity and is especially used as an anti-inflammatory and anti-allergic drug. Topically, it is employed in the treatment of glucocorticoid-responsive dermatoses. Systemically, dexamethasone decreases the incidence and severity of hearing loss consequent to bacterial meningitis. Its systemic glucocorticoid potency is about 25 times that of cortisone. Dexamethasone is capable of inducing all the usual side effects of adrenal corticoids, except that the mineralocorticoid-like side effects are less pronounced than with cortisone acetate.

Also, glucocorticoids as a group are the most useful class of drugs for treating many eosinophil-related disorders. Glucocorticoids, e.g., dexamethasone, methylprednisolone and hydrocortisone, produce eosinopenia in normal persons, decrease circulating eosinophils in patients with eosinophilia, and reduce eosinophil influx at inflammatory sites (Butterfield et al., Anti-inflammatory Steroid Action: Basic and Clinical Aspects, Schleimer et al., eds., Academic Press, Inc., (1989) at page 151). In 1991, Wallen et al. (*J. Immunol.*, 147, 3940 (1991)) reported the dose-dependent inhibition of IL-5-mediated eosinophil survival by dexamethasone, methylprednisolone and hydrocortisone. Moreover, they disclosed that dexamethasone produced a dose-dependent increase in the $EC_{50}$ for IL-5-mediated viability enhancement. The relative eosinophil viability inhibitory potencies of the glucocorticoids tested correlated with previously described anti-inflammatory potencies and with the affinities of these agents for the glucocorticoid receptor in the following order: dexamethasone>methylprednisolone>hydrocortisone.

2.3 Bupivacaine

Bupivacaine was introduced in 1963, and is a widely used amide local anesthetic; its structure is similar to that of lidocaine, except the amine-containing group is a butyl piperidine. It is a potent agent capable of producing prolonged anesthesia. Its long duration of action plus its tendency to provide more sensory than motor block has made it a popular drug for providing prolonged analgesia during labor or postoperative period. By taking advantage of indwelling catheters and continuous infusions, bupivacaine can be used to provide several days of effective analgesia.

Local anesthetics such as bupivacaine block the generation and the conduction of nerve impulses, presumably by increasing the threshold for electrical excitation in the nerve, by slowing the propagation of the nerve impulse, and by reducing the rate of rise of the action potential. In general, the progression of anesthesia is related to the diameter, myelination and conduction velocity of affected nerve fibers. Clinically, the order of loss of nerve function is as follows: (1) pain, (2) temperature, (3) touch, (4) proprioception, and (5) skeletal muscle tone. Systemic absorption of local anesthetics produces effects on the cardiovascular and central nervous systems. At blood concentrations achieved with therapeutic doses, changes in cardiac conduction, excitability, refractoriness, contractility, and peripheral vascular resistance are minimal. However, toxic blood concentrations depress cardiac conduction and excitability, which may lead to atrioventricular block, ventricular arrhythmias and to cardiac arrest, sometimes resulting in fatalities. In addition, myocardial contractility is depressed and peripheral vasodilation occurs, leading to decreased cardiac output and arterial blood pressure.

Bupivacaine is more cardiotoxic than equieffective doses of lidocaine. Clinically, this is manifested by severe ventricular arrhythmias and myocardial depression after inadvertent intravascular administration of large doses of bupivacaine. The enhanced cardiotoxicity of bupivacaine probably is due to multiple factors. Lidocaine and bupivacaine both block cardiac $Na^+$ channels rapidly during systole. However, bupivacaine dissociates much more slowly than does lidocaine during diastole, so a significant fraction of $Na^+$ channels remains blocked at the end of diastole (at physiological heart rates) with bupivacaine. Thus the block by bupivacaine is cumulative and substantially more than would be predicted by its local anesthetic potency. At least a portion of the cardiac toxicity of bupivacaine may be mediated centrally, as direct injection of small quantities of bupivacaine into the medulla can produce malignant ventricular arrhythmias. Bupivacaine induced cardiac toxicity can be very difficult to treat, and its severity is enhanced in the presence of acidosis, hypercarbia, and hypoxemia. Clinical reports and animal research suggest that cardiovascular changes are more likely to occur after unintended intravascular injection of bupivacaine. Therefore incremental dosage is crucial.

As potent drugs such as corticosteroids may induce unwanted side effects if administered in unsafe doses, methods of detecting and/or quantifying these compounds, optionally in the presence of other compounds, accurately and rapidly are still needed. For this purpose, the present invention combines the detection methods of high performance liquid chromatography and mass spectrometry to substantially simultaneously detect relatively small amounts of corticosteroids in the form of adducts in the presence of other drug agents.

2.4 Liquid and Mass Spectroscopy

LC/MS systems, which combine high performance liquid chromatography (HPLC) and mass spectrometry (MS), are used for several purposes including 1) environmental studies, for example, to evaluate water, soil and waste; 2) food analysis, to identify contaminants and adulterants; 3) pharmaceutical development, to analyze natural and synthetic products; and 4) life sciences, to characterize protein components.

2.4.1 Liquid Chromatography

Liquid chromatography is a technique for separating components in a sample mixture. At any given time during separation, some molecules of a component are adsorbed to a stationary solid support, while other molecules are dissolved in a liquid solvent flowing past the solid support. The adsorbed molecules are said to be in a "stationary phase" while the dissolved molecules are said to be in a "mobile phase." Separation is based upon the differences of the components' chemical and/or physical properties. Sample components can differ significantly in their solubility in a given solvent. Specifically, nonpolar components tend to dissolve more readily in organic solvents, while polar components tend to dissolve more readily in water. To accommodate samples with both polar and nonpolar component, reverse-phase gradient-elution liquid chromatography (GELC) provides for a gradual transition of organic solvent to water as the liquid solvent in an LC system.

At equilibrium, the rate at which a component's molecules in the stationary phase are released to the mobile phase equals the rate at which the same component's molecules in the mobile phase are adsorbed to the stationary phase. For each component, the ratio of the number of molecules in the stationary phase to the number of molecules in the mobile phase is quantified by a partitioning coefficient. This partitioning coefficient thus corresponds to the average percentage of time the molecules of a component are in the mobile phase. This percentage correlates with the mobility of the component past the solid support. Sample components with different mobilities separate, as they progress past the solid support. With sufficient separation, the components emerge serially in the chromatography effluent.

To complete the analysis of a sample mixture, the eluting components need to be identified and quantified. Various types of detectors, for example, ultra-violet absorption detectors positioned to monitor the ultraviolet absorption characteristics of the effluent, can be used to detect eluting components. Since each component has a characteristic retention time in a chromatographic column, the time of detection is often used for component identification, while the degree of ultraviolet absorption can be used to quantify the component.

However, it is often not possible to identify and quantify sample components dissolved in the chromatography effluent. Some components are not readily detectable, others appear in quantities too small to measure reliably, and others can not be uniquely identified by their retention times. In these situations, and others, a mass spectrometer can be used for sample component identification and quantification.

2.4.2 Mass Spectroscopy

Mass spectrometry (MS) has long been a widely accepted analytical technique for obtaining qualitative and quantitative information from a sample. MS is commonly used to determine molecular weight, identify chemical structures, and accurately determine the composition of mixtures. A mass spectrometer provides a mass spectrum of a sample component by separating sample subcomponents according to molecular mass and quantifying the number of subcomponent molecules for each molecular mass. Mass spectrometers typically operate by ionizing sample molecules and then sweep-filtering the resulting ions according to their charge-to-mass ratios. To minimize interference with ion movement through the mass filter, mass spectrometers operate under vacuum conditions. MS is becoming increasingly important in biological research to determine the structure of organic molecules based on the fragmentation pattern of ions formed when sample molecules are ionized.

The coupling of mass spectrometers with liquid chromatography systems is a valuable tool for identifying organic compounds. Liquid chromatographic separation systems provide the ability to separate solutions containing mixtures of organic compounds into liquid fractions containing individual compounds. The product of the liquid chromatographic column is an eluant liquid solution of the compound or compounds to be analyzed that is at atmospheric pressure, whereas the mass spectrometer analyzes compounds in a high vacuum system. However, evaporation of the eluant solvent and presentation of the desolvated particles to the mass spectrometer in a suitable form has presented serious difficulties limiting the sensitivity of the mass spectrometer and greatly complicating its efficient operation. Clearly, there is a need for a superior process for detecting trace amounts of cortiocosteriods.

3. SUMMARY OF THE INVENTION

The present invention encompasses a method of detecting a corticosteroid in a sample by adding an internal standard to a sample suspected of containing a corticosteroid; removing, if necessary, interfering compounds from the sample; placing the sample on an HPLC column equilibrated with a $NH_4OAc:MeOH$ solution and collecting an eluent; and analyzing the eluent of the HPLC column with a MS, wherein if contained in the sample, the corticosteroid forms an adduct that is detected by the MS. In one embodiment, the corticosteroid is aldosterone, beclomethasone, betamethasone, corticosterone, cortisol, cortisone, dexamethasone, fludrocortisone, flumethasone, hydrocortisone, 6α-methylprednisolone, 6β-methylprednisolone, paramethasone, prednisolone, prednisone, prednylidene, 4-pregnene-20,21-diol-3,11-diol, presesterone, testosterone, triamcinolone, or mixtures thereof, preferably, the corticosteroid is beclomethasone, dexamethasone, flumethasone, or mixtures thereof.

In another embodiment of the invention, the internal standard is beclomethasone, $d^3$-bupivacaine, $d^9$-bupivacaine, flumethasone, pentylcaine, or mixtures thereof.

In yet another embodiment of the invention, in addition to a corticosteroid, at least one drug agent is present which optionally is quantified. In one embodiment, the drug agent is bupivacaine.

In another embodiment of the invention, the interfering compounds are inorganic salts, organic materials, physiological materials, or combinations thereof. The interfering compounds are removed using liquid—liquid extraction, solid phase extraction, protein precipitation, or a combination thereof, preferably solid phase extraction.

In another embodiment of the invention, the HPLC column is packed with a low acid silica stationary phase. The $NH_4OAc:MeOH$ solution has a concentration of 0.5 mM to about 10 mM $NH_4OAc$ in MeOH and $H_2O$.

In yet another embodiment of the invention, the MS has a desolvation temperature of about 250° C. to about 450° C. The MS has a source block temperature of about 80° C. to about 150° C. The MS has a desolvation gas flow rate of about 400 l/h to about 860 l/h.

In another embodiment of the invention, the method further comprises quantifying the amount of corticosteroid wherein the peak height of the corticosteroid is quantified using a calibration curve. The calibration curved is obtained by plotting data points of known concentrations of corticosteroid versus a peak height ratio of a known amount of corticosteroid/internal standard. Preferably, the calibration curve has from about 4 to about 9 data points.

3.1 Definitions

As used herein, unless otherwise specified, the term "lower limit of quantification" or "LLOQ" means the lowest non-zero amount of corticosteroid detectable by a LC/MS system.

As used herein, unless otherwise specified, the term "upper limit of quantification" or "ULOQ" means the highest amount of corticosteroid detectable by a LC/MS system.

As used herein, unless otherwise specified, the term "adduct" means a corticosteroid cluster formed by the addition of another molecule or part of a molecule, such as acetate, to a corticosteroid. The cluster may or may not have a charge. The cluster may be formed by any means known in the art including, but not limited to, ionic bonds, covalent bonds, hydrogen bonds, electric forces, and combinations thereof.

As used herein, unless otherwise specified, the term "drug agent" includes, but is not limited to, a substance used, or potentially used, in the diagnosis, treatment, or prevention of a disease or as a component of a medication. The drug agent may optionally be one administered to patients in conjunction with corticosteroids. Optionally, these drug agents may be detected and quantified substantially simultaneously with the corticosteroid.

As used herein, unless otherwise specified, the term "interfering compound" includes, but is not limited to, compounds within an analytical sample that hinder, obstruct, or impede one of skill in the art from detecting the corticosteroid and/or other drug agents of interest, such as for example, compounds which are structurally similar to a corticosteroid, or compounds which have the same or similar chromatography retention times with the corticosteroid. Optionally, interfering compounds within a sample that may be removed using extraction methodology prior to analyzing the sample.

As used herein, unless otherwise specified, the term "remove" means eliminating or reducing the amount of interfering compounds from a sample in an amount sufficient to reduce or avoid unwanted or overlapping peaks or readings within a HPLC or MS chromatogram which affect detection.

As used herein, unless otherwise specified, the term "LC/MS/MS" or "LC/MS" means either a multiple analytical apparatus having a liquid chromatography and mass spectrometry or separate liquid chromatography and mass spectrometry apparatus used in sequential order, but not necessarily immediately thereafter.

As used herein, unless otherwise specified, the term "substantially simultaneously" means, detecting or quantifying at least two compounds within one sample either sequentially or at the same time.

As used herein, unless otherwise specified, the term "acetate containing solution" includes, but is not limited to solutions of organic solvents, non-organic solvents, or both, having acetate ions.

4. BRIEF DESCRIPTION OF THE FIGURES

5. DETAILED DESCRIPTION OF THE INVENTION

Figure 1:
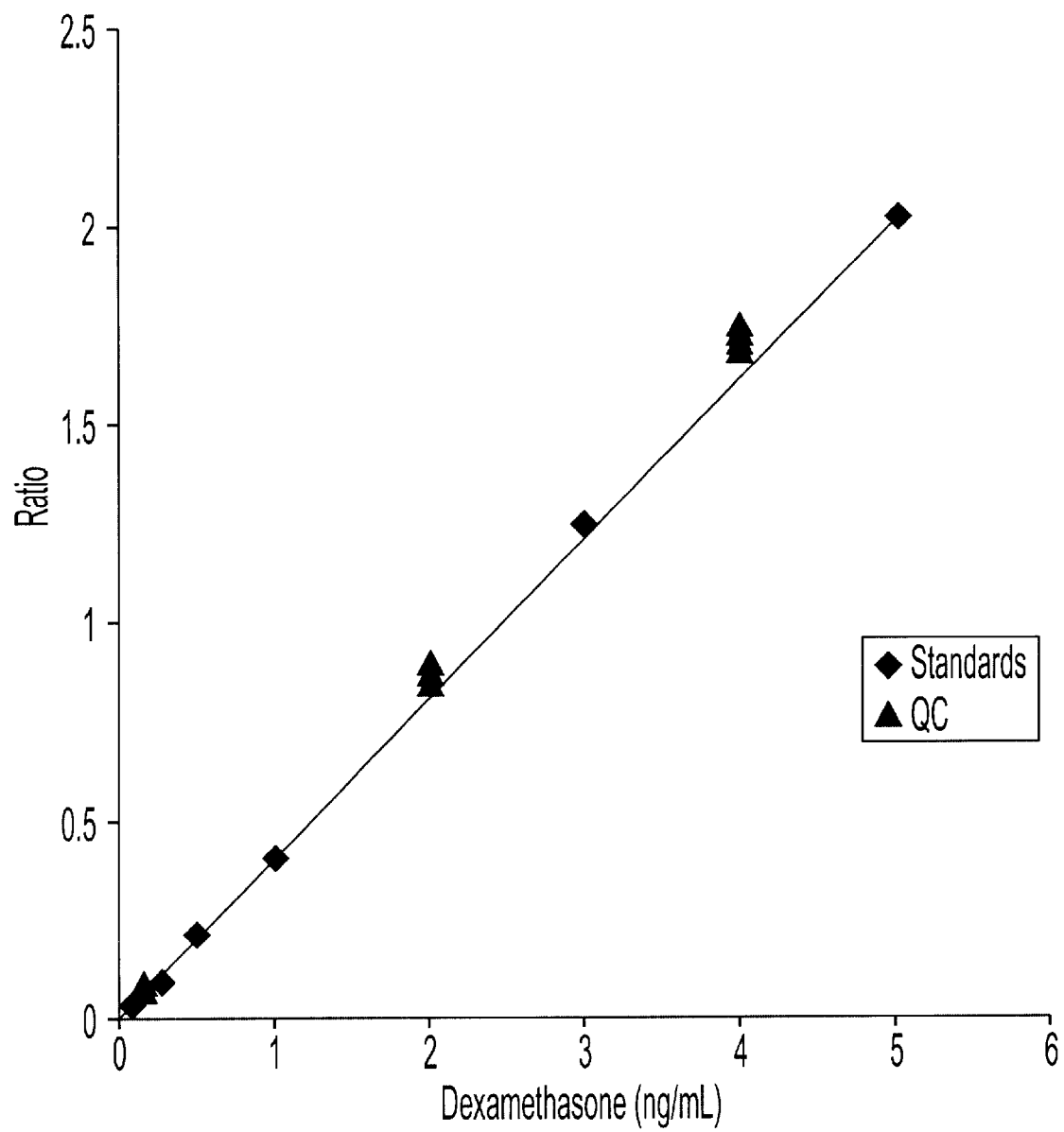
FIG. 1 illustrates a dexamethasone calibration curve in plasma.

Hormonal steroids, such as corticosteroids, are naturally present in an organism. Traditional techniques for hormonal quantification are hampered by interference of other naturally occurring steroids. The methods of the present invention overcome the deficiencies of the traditional techniques by separating interfering compounds using HPLC and selectively detecting and/or quantifying the targeted hormone using MS.

The present invention encompasses methods of detecting and/or quantifying corticosteroids by forming an adduct and detecting the adduct using a LC/MS/MS system. In a preferred embodiment, the method detects corticosteroid-acetate adducts in the presence of interfering compounds or drug agents. In a more preferred embodiment, the method of the present invention substantially detects and/or quantifies a corticosteroid-acetate adduct within a biological fluid, such as human plasma. In an even more preferred embodiment, the method detects and/or quantifies dexamethasone-acetate adducts. In a most preferred embodiment, the method detects and quantifies dexamethasone in an amount as low as about 50 pg/ml.

Natural steroids show very weak signal response in electron spray ionization (ESI) and atmospheric pressure chemical ionization (APCI) of a MS, thereby reducing detection sensitivity of corticosteroids. Without being limited by theory, the method of the present invention is based on the discovery that corticosteroids form a detectable adduct in the presence of acetate ions. The presence and amount of the corticosteroid-acetate adduct can be determined using a combination of high performance liquid chromatography (HPLC) and mass spectrometry (MS). For example, a corticosteroid, such as dexamethasone, in the presence of an acetate source, such as ammonium acetate, sodium acetate, potassium acetate, calcium acetate, forms a corticosteroid-acetate adduct which can be detected using MS. One of skill in the art is presumed to understand that any solution that has acetate ions that can form an adduct is a suitable solvent. When the corticosteroid is dexamethasone, the adduct is observed at $[M+59]^-$ $[M+OAc]^-$. Unlike prior methods that may include only one detection method or weak detection methods, the method of the present application detects trace amounts of corticosteroids. This is true even where other drug agents are present at much higher concentrations relative to the corticosteroid. For example, dexamethasone may be detected when present in a concentration of only about 0.04% by weight of a bupivacaine-dexamethasone solution. Other drug agents include, but are not limited to, morphine, morphine analogs, hydromorphone, hydrocodone, oxycodone, naltrexone, naloxone, bupreienorphine, etc. Accordingly, when using this method the presence of corticosteroids can be determined in concentrations as low as about 50 pg/ml.

5.1 Method of Detecting Corticosteroids

The methods of the present invention detect corticosteroids within a sample, said sample includes, but is not limited to, compositions, solutions, or biological fluids. The corticosteroid is detected by forming a corticosteroid adduct, preferably, a corticosteroid-acetate adduct, and measuring the presence of the adduct using high performance liquid chromatography and mass spectrometry. In a preferred method the corticosteroid is detected concurrently with the detection of at least one drug agent. In a more preferred method, the corticosteroid is detected at concentrations as low as about 50 pg/ml. The method comprises the steps of preparing a sample containing or suspected of containing a corticosteroid, removing interfering materials, reconstituting the sample, passing the reconstituted sample through a HPLC column equilibrated with at least one acetate ion source and subsequently, measuring the presence and/or amount of the corticosteroid within the sample using mass spectrometry.

Sample preparation comprises the following steps. A sufficient amount of sample known or suspected of having a corticosteroid is allowed to warm to room temperature. In one embodiment, the sample comprises a biological fluid, which includes, but is not limited, to plasma such as human plasma, which optionally may not be tested at the same location where the sample is gathered. Consequently, the sample may be transported by any means known to the skilled artisan. Typically, human plasma is transported at a temperature of about −40° C. to about 0° C., preferably human plasma is transported at a temperature of about −30° C. to about −10° C., and more preferably a human plasma sample is transported at a temperature of about −25° C. to about −15° C. Typically, the corticosteroid are aldosterone, beclomethasone, betamethasone, corticosterone, cortisol, cortisone, dexamethasone, fludrocortisone, flumethasone, hydrocortisone, 6α-methylprednisolone, 6β-methylprednisolone, paramethasone, prednisolone, prednisone, prednylidene, 4-pregnene-20,21-diol-3,11-diol, presesterone, testosterone, triamcinolone, among others. Preferably, the corticosteroid is beclomethasone, dexamethasone, flumethasone, hydrocortisone, prednisolone, presesterone, testosterone, or combinations thereof. More preferably, the corticosteroid is beclomethasone, dexamethasone, flumethasone, and combinations thereof, and most preferably, the corticosteroid is dexamethasone.

Once the sample is allowed to warm to room temperature, the sample is mixed and placed in a centrifuge for about 10 min to about 30 minutes, preferably for about 20 min at about 3000 rpm to about 3500 rpm, preferably about 3200 rpm and at a temperature of about 0° C. to about 10° C., preferably about 5° C. To about 500 μl of the sample, an internal standard is added in an amount of about 50 μl to about 400 μl, preferably, about 100 μl to about 350 μl, and more preferably in an amount of about 150 μl to about 300 μl. After mixing the sample with the internal standard, an adequate amount of the same is transferred to at least one well of a collection plate. Typical sample portions include amounts of about 700 μl (500 μl of sample and 200 μl of internal standard). Optionally, more than one sample may be tested using automation apparatus commonly known in the art.

The internal standard may be at least one compound of known concentration and MS peak. The internal standard typically comprises compounds such as beclomethasone, $d^3$-bupivacaine, $d^9$-bupivacaine, flumethasone, pentylcaine, or other compounds known in the art. The concentration of the internal standard typically is in an amount of about 1 ng/ml to about 100 ng/ml, preferably, about 5 ng/ml to about 50 ng/ml in a suitable solvent. Suitable solvents include, but are not limited to, methanol, acetonitrile, distilled water, and mixtures thereof.

Interfering materials may interfere with corticosteroid detection. Interfering materials include, inorganic salts, organic materials such as proteins, corticosteroids other than the target compound, and physiological materials such as red or white blood cells, and the like. The interfering materials are removed from the sample by any means commonly used in the art, for example, extraction such as solid phase extraction (SPE), liquid—liquid extraction, protein precipitation, etc. SPE extraction apparatus include, but are not limited to, those manufactured by Tomtec (Hamden, Conn.), Gilson, Inc. (Middleton, Wis.), and Varian, Inc. (Palo Alto, Calif.), among others.

Under SPE conditions, the sample, dissolved in a suitable solvent, is absorbed onto a solid phase sorbent, including, but not limited to, C-18 sorbent, ion exchange resin, solid phase sorbent such as MPC® manufactured by 3M, or mixtures thereof. Target compounds and internal standards are absorbed onto the solid phase and interfering compounds are removed by washing with a suitable washing solvent. Suitable washing solvents, include, but are not limited to, acetonitrile, water, methanol, or a combination thereof.

Under the SPE conditions the sample is dissolved in a suitable solvent, such as a solvent wherein the sample is insoluble including, but not limited to, water or water with an organic solvent. For example, the extraction plate is conditioned with acetonitrile, followed by applying a vacuum, MeOH, and deionized water, and a second vacuum is applied but not to dryness. Thereafter, the sample is loaded onto the conditioned extraction plate. Typically, the sample is dissolved in about 200 μl of acetonitrile, and a vacuum is applied to dryness. The sample is loaded and washed with deionized water and a vacuum is applied to dryness, followed by a second wash of a solution of about 1% to about 40% MeOH in deionized water, preferably about 5% to about 15% MeOH in deionized water and most preferably 10% MeOH in deionized water, and a second vacuum is applied to dryness. Subsequently, the sample is eluted with acetonitrile and a vacuum is applied to dryness, this step is typically performed twice, and optionally, the eluents may be combined to form a single sample.

The sample as an elution block is dried under a flow of nitrogen. A skilled artisan with little or no experimentation can easily determine necessary temperature and time needed to dry any sample. Typically, the sample is dried at a temperature of about 40° C. for about 30 min. Subsequently, the sample is reconstituted in $H_2O$/MeOH solution in a ratio of about 1:1, preferably about 10:1, and most preferably about 4:1, mixed, and injected into the LC/MS system.

The HPLC system comprises a silica packed column equilibrated with at least one acetate source solvent and at least one alcohol. Preferably, the column is packed with a low acid silica stationary phase column such as Zorbax® manufactured by Agilent Technologies (Wilmington, Del.), columns manufactured by Vydac® (Hesteria, Calif.), Nucelosil® manufactured by Macherey-Nagel GmbH (Germany), Nova-Pak®, μBondapak®, YMCbasic™ manufactured by Waters Corp. (Milford, Mass.), among others. Preferably, the silica column is Zorbax® SB-C18 StableBond®. The HPLC mobile phase includes acetate ion sources such as, but is not limited to, $NH_4OAc$, and alcohols such as methanol, ethanol, isopropanol, and combinations thereof. Typically, the acetate source solvent is dissolved within an alcohol solvent in a concentration of about 0.5 mM to about 10 mM, preferably from about 1 mM to about 8 mM, and more preferably from about 2 mM to about 6 mM.

A skilled artisan with little or no experimentation can easily determine the flow rates for the HPLC solvent system depending on the configuration of the HPLC system, and the amount and concentration of the sample.

After the sample is injected onto the HPLC, the sample is analyzed using a MS. The typical settings for the MS include a desolvation temperature of about 250° C. to about 450° C., preferably a temperature of about 350° C. to about 420° C., and more preferably a temperature of about 380° C. to about 410° C. The typical source block temperature is from about 80° C. to about 150° C., preferably from about 95° C. to about 120° C., and more preferably from about 100° C. to about 110° C. A skilled artisan with little or no experimentation can easily determine the flow rates for the MS desolvation gas. Typically, the desolvation gas flow rates are from about 400 l/h to about 860 l/h, preferably from about 650 l/h to about 750 l/h.

To quantify the amount of corticosteroid within a sample, a calibration curve is created by measuring the peak area ratio of a known target compound/internal standard of a sufficient amount of standard samples of known concentration using MS. The concentrations of the standard samples are typically of different known concentrations ranging from LLOQ to ULOQ. Each standard has a known amount of a target compound and a constant amount of an internal standard, thereafter, a calibration curve is plotted using the known target compound/internal standard peak ratio. Each calibration curve comprises about 4 to about 9 data points. Preferably, each calibration curve comprises about 5 to about 7 data points. Using the calibration curve, the concentration of at least one target compound is determined by comparing the sample peak area ratio of the target compound/internal standard with the calibration curve.

The method for quantification was validated using Micromass Quattro LC and Micromass Ultima mass spectrometers coupled with HPLC systems. During validation runs, the mean linearity ($r^2$) after three days for dexamethasone was 0.9996. The CV of the LOQ Quality Control (QC), QC Low, QC mid, and QC high was 10.3%, 4.36%, 2.43%, and 1.99%, respectively. The quantification range for dexamethasone was from 0.05 ng/ml to about 5 ng/ml.

FIG. 1 represents a calibration curve for samples having a known amount of dexamethasone in plasma. The plot represents the relationship of the known dexamethasone concentration versus the MS peak area ratio of known sample/internal standard. The cubes represent the standard samples and the triangles represent the quality control samples. The samples were prepared using the methodology described above, and the concentrations as represented in Table I.

TABLE I

Data for Calibration Curve for Dexamethasone

| Run | Sample Concentration | | | |
|---|---|---|---|---|
| | 0.0501 (ng/ml) | 0.15 (ng/ml) | 2 (ng/ml) | 4 (ng/ml) |
| 1 | 0.0426 | 0.166 | 2.10 | 4.24 |
| 2 | 0.0422 | 0.149 | 2.16 | 4.17 |
| 3 | 0.0411 | 0.161 | 2.16 | 4.34 |
| 4 | 0.0402 | 0.158 | 2.20 | 4.22 |
| 5 | 0.0414 | 0.145 | 2.10 | 4.29 |
| 6 | 0.0580 | 0.143 | 2.21 | 4.27 |
| 7 | 0.0517 | 0.154 | 2.06 | 4.09 |
| 8 | 0.0535 | 0.161 | 2.13 | 4.05 |
| 9 | 0.0485 | 0.164 | 2.13 | 4.10 |
| 10 | 0.0496 | 0.161 | 2.13 | 1.12 |
| 11 | 0.0510 | 0.152 | 2.21 | 4.11 |

TABLE I-continued

Data for Calibration Curve for Dexamethasone

| Run | Sample Concentration | | | |
|---|---|---|---|---|
| | 0.0501 (ng/ml) | 0.15 (ng/ml) | 2 (ng/ml) | 4 (ng/ml) |
| 12 | 0.0517 | 0.155 | 2.05 | 4.09 |
| 13 | 0.0462 | 0.157 | 2.16 | 4.30 |
| Std. Deviation | 0.0469 | 0.156 | 2.13 | 4.18 |
| Mean | 0.005 | 0.006 | 0.05 | 0.09 |

Figure 2:
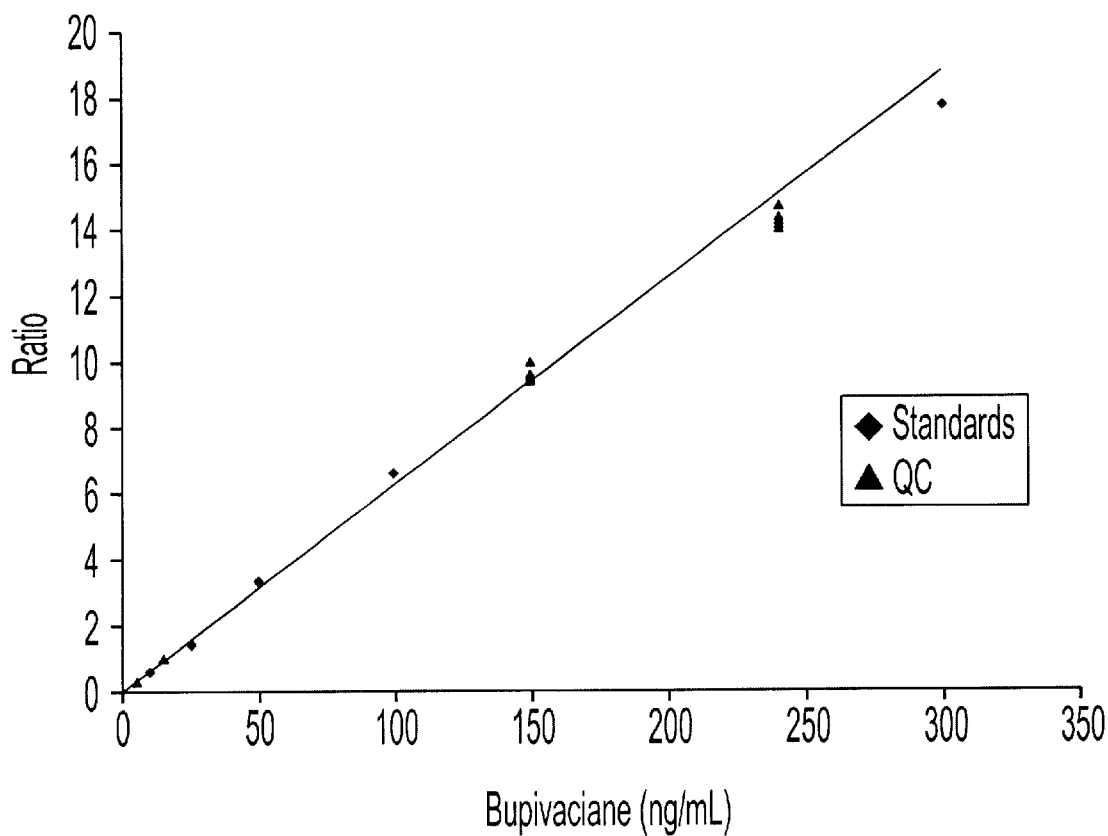
FIG. 2 illustrates a bupivacaine calibration curve in plasma.

FIG. 2 represents a calibration curve for samples having a known amount of bupivacaine in plasma. The plot represents the relationship of the known bupivacaine concentration versus the MS peak area ratio of the known sample/internal standard. The cubes represent the standard samples and the triangles represent the quality control samples. The samples were prepared using the methodology described above, and concentrations as represented in Table II.

TABLE II

Calibration Curve for Bupivacaine

| Run | Sample Concentration | | | |
|---|---|---|---|---|
| | 5 (ng/ml) | 15 (ng/ml) | 150 (ng/ml) | 240 (ng/ml) |
| 1 | 5.34 | 16.9 | 153 | 224 |
| 2 | 5.52 | 15.8 | 153 | 226 |
| 3 | 5.45 | 16.6 | 154 | 231 |
| 4 | 5.41 | 16.8 | 159 | 229 |
| 5 | 5.16 | 16.8 | 152 | 236 |
| 6 | 5.32 | 16.5 | 151 | 228 |
| 7 | 5.57 | 16.7 | 158 | 237 |
| 8 | 6 | 17.3 | 165 | 240 |
| 9 | 5.4 | 16.2 | 169 | 237 |
| 10 | 5.63 | 16.2 | 156 | 238 |
| 11 | 5.68 | 16.5 | 167 | 245 |
| 12 | 5.56 | 16.4 | 155 | 244 |
| mean | 5.56 | 16.6 | 157 | 234 |
| std deviation | 0.19 | 0.34 | 5.4 | 5.9 |

Figure 3:
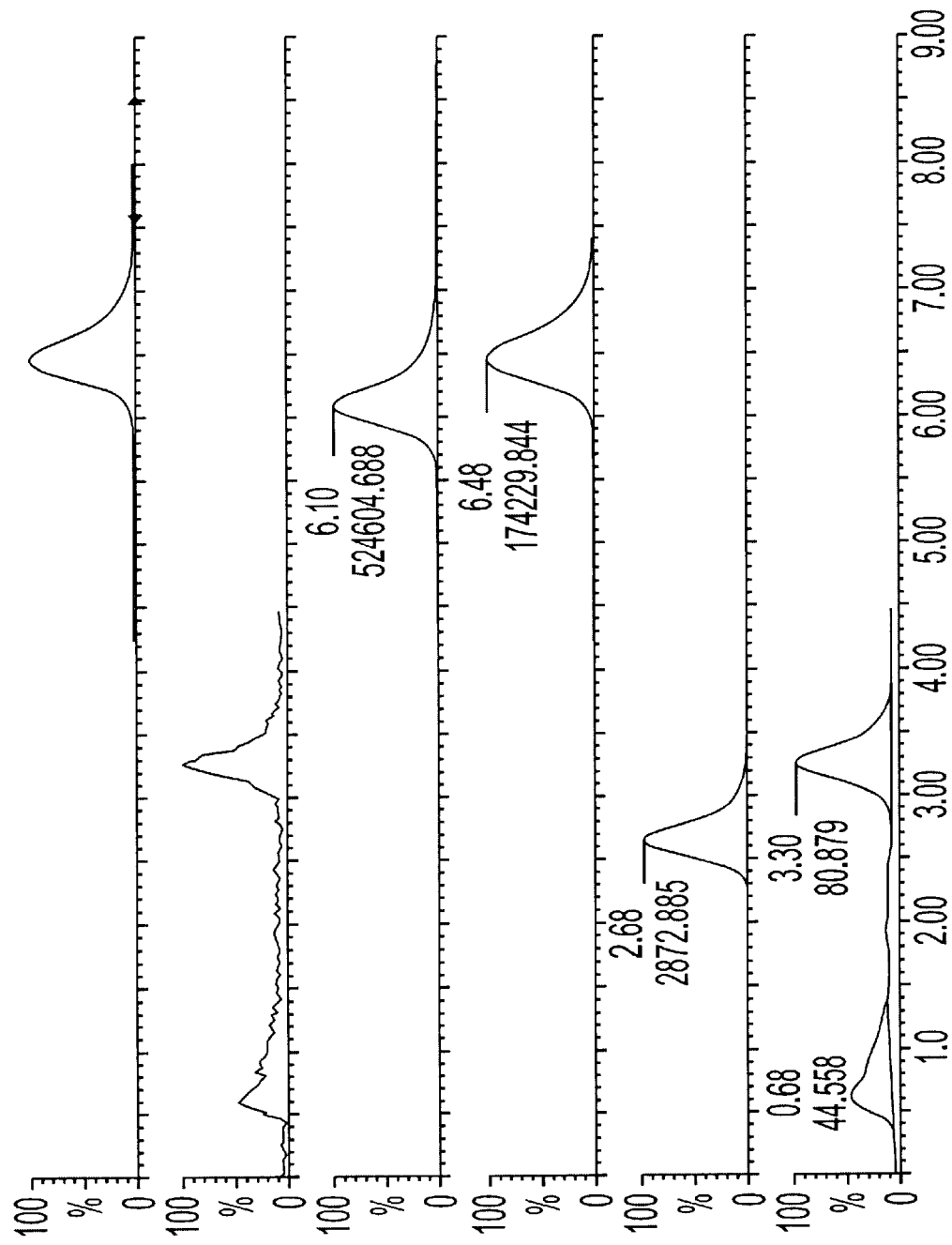
FIG. 3 illustrates the identification of a sample with a known concentration of dexamethasone and bupivacaine.

FIG. 3 illustrates the identification of a plasma sample having a known concentration of dexamethasone (50 pg/ml) and bupivacaine (5 ng/ml). The sample having dexamethasone and bupivacaine was analyzed as described above. Lines 1 and 2 represent the chromatogram of the sample which were compared to known chromatograms for $d^9$-bupivacaine (line 3), bupivacaine (line 4), flumethasone (line 5), and dexamethasone (line 6). A comparison of lines 1 and 4 indicates that the peak in line 1 has the same retention time value as the peak of line 4, i.e. a retention time of 6.48 min. A comparison of lines 2 and 6 indicates that the peaks in line 2 have the same retention time value as the peaks of line 6, i.e. 0.68 min and 3.3 min. Consequently, as the retention time values of the peaks of lines 3 and 5 are not identical to those of lines 1 and 2, it can be ruled out that the sample does not contain either $d^9$-bupivacaine or flumethasone.

6. EXAMPLES

Certain embodiments of the invention, as well as certain novel and unexpected advantages of the invention, are illustrated by the following non-limiting examples.

6.1 Detection of Dexamethasone and Bupivacaine in Human Plasma

6.1.1 Materials and Methods

6.1.1.1 Materials and Apparatus

Dexamethasone and bupivacaine were purchased from Sigma® (St. Louis, Mo.). The 3M Empore™ High Performance Extraction Disk plates (C18) with standard density 96-well were manufactured by 3M Filtration Products (St. Paul, Minn.). HPLC grade methanol and acetonitrile and reagent grade ammonium acetate were purchased from either Burdick & Jackson (Muskegon, Mich.) or Mallinckrodt Laboratory Chemicals, a Division of Mallinckrodt Baker, Inc. (Phillipsburg, N.J.). Deionized water having a conductivity of 18.2 MΩ was obtained from a Miller Q Plus™ water system manufactured by Miller Poll Corp.

Solutions of $NH_4OH$, $NH_4OH/MeOH$ were prepared as follows. Ammonium acetate (0.154 g, 2 mmol) was dissolved and mixed in 1000 ml of deionized water to obtain a 2 mM solution of $NH_4OAc$. A $MeOH:NH_4OAc$ solution was prepared by mixing 600 ml of MeOH into 400 ml of 2 mM $NH_4OAc$ to obtain a 3:2 $MeOH:NH_4OAc$ solution. Ammonium acetate (0.616 g, 8 mmol) was dissolved in 1000 ml of deionized water to obtain a 8 mM solution of $NH_4OAc$.

Internal standard solutions were prepared as follows. Flumethasone (10 mg, 0.02 mmol) was dissolved in 5 ml of MeOH and diluted to 100 ml with deionized water/MeOH 4:1 solution. This solution was labeled FluA at a concentration of 100 µg/ml. The FluA solution (0.5 ml) was diluted to a volume of 50 ml with a deionized water/MeOH 4:1 solution to obtain a solution labeled FluB at a concentration of 1 µg/ml. $d^9$-Bupivacaine (10 mg, 0.03 mmol) was dissolved in 5 ml of MeOH and diluted to 100 ml with a deionized water/MeOH 4:1 solution. This solution was labeled BvdA at a concentration of 100 µg/ml. The BvdA solution (0.5 ml) was diluted to a volume of 50 ml with a deionized water/MeOH 4:1 solution to obtain a solution labeled BvdB at a concentration of 1 µg/ml.

The mass spectrometer was a Micromass, Quatro LC LC/MS/MS system manufactured by Micromass LTD (Manchester, United Kingdom). The data was analyzed using Masslyn version 3.3 software. The liquid chromatograph is a Waters Alliance HT Separation Module 2790 manufactured by Waters Corp. (Milford, Mass.).

6.1.1.2 Methodology

A plasma sample (0.7 ml) is allowed to warm to room temperature (~25° C.). The sample is mixed, placed on a centrifuge for 20 min at 3200 rpm, and cooled to 5° C. 500 µl of the plasma sample is placed into a 12×75 mm test tube and 200 µl of an internal standard (5 ng/ml of flumethasone and 50 ng/ml of $d^9$-bupivacaine) is added. The plasma sample is mixed and 700 µl of the sample is placed in a 96-well collection plate. The sample is extracted using a solid phase extraction apparatus.

The solid phase extraction is performed on 3M Empore™ High Performance Extraction Disk plates (C18) with standard density 96-well as follows. The sorbent in each well is conditioned sequentially with 200 µl acetonitrile, 100 µl of MeOH, and then 200 µl of deionized water. The sample (700 µl) is loaded and a vacuum is applied until the sample is placed onto the sorbent. The absorbed sample is washed sequentially with 400 µl of deionized water and 400 µl of 10% MeOH in deionized water and a vacuum is applied. The sample is twice eluted with 200 µl of acetonitrile and twice reduced in volume under vacuum. The acetonitrile elutions are combined and the acetonitrile is removed by evaporation under a nitrogen gas flow at 40° C. for 30 min. The sample is reconstituted with 100 µl of $H_2O/MeOH$ (4:1), and injected (35 µl) into the LC/MS system.

The HPLC parameters are described in Table III. The MS parameters are described in Table IV.

TABLE III

HPLC Parameters

| | |
|---|---|
| HPLC column type | Zorbax SB C18 |
| Column Length | 50 mm |
| Column Diameter | 2.1 mm |
| HPLC Mobile phase | MeOH: $NH_4OAc$ (2 mM in water) 3:2 |
| Flow rate | 0.2 ml/min. |
| Run time | 9 min. |

TABLE IV

MS Parameters

| | |
|---|---|
| MS Desolvation temperature | 400° C. ± 20° C. |
| MS Source block temperature | 100° C. ± 10° C. |
| MS Ionization mode | ESI |
| Desolvation gas | 810 ± 30 l/h |
| Nebulizer gas | 110 l/h |

6.2 Standardization Curves

6.2.1 Materials and Methods

Flumethasone and $d^9$-bupivacaine were purchased from Sigma®. The flumethasone stock solution was prepared by dissolving 10 mg in about 5–10 ml MeOH in a vial, and then transferring the dissolved flumethasone into a 100 ml volumetric flask. The solution was diluted to 100 ml using a deionized water/MeOH (4:1) solution. Using successive dilutions, a series of samples of known concentrations were made as described in Table V.

TABLE V

Flumethasone Stock Solutions for calibration curves

| Stock Solution | Concentration | Volume used | Diluted Volume | New Stock Solution |
|---|---|---|---|---|
| | 10 mg | | 100 ml | Flu-1 (100 µg/ml) |
| Flu-1 | 100 µg/ml | 0.5 ml | 50 ml | Flu-2 (1 µg/ml) |

The dexamethasone stock solution was prepared by dissolving 20 mg of sample in about 5–10 ml MeOH in a vial, and then transferring the dissolved dexamethasone into a 200 ml volumetric flask. The solution was diluted to 200 ml using a deionized water/MeOH (4:1) solution. Using successive dilutions, a series of samples of known concentrations were made as described in Table VI.

TABLE VI

Dexamethasone Stock Solutions for calibration curves

| Stock Solution | Concentration | Volume used | Diluted Volume | New Stock Solution |
|---|---|---|---|---|
|  | 20 mg |  | 200 ml | Dex-1 (100 µg/ml) |
| Dex-1 | 100 µg/ml | 5 ml | 50 ml | Dex-2 (10 µg/ml) |
| Dex-2 | 10 µg/ml | 5 ml | 50 ml | Dex-3 (1 µg/ml) |
| Dex-3 | 1 µg/ml | 5 ml | 50 ml | Dex-4 (100 ng/ml) |
| Dex-4 | 100 ng/ml | 5 ml | 50 ml | Dex-5 (10 ng/ml) |
| Dex-5 | 10 ng/ml | 5 ml | 50 ml | Dex-6 (1 ng/ml) |

$d^9$-Bupivacaine was purchased from Radian International (Austin, Tex.). The $d^9$-bupivacaine stock solution was prepared by dissolving 10 mg of sample in about 5–10 ml MeOH in a vial, and then transferring the dissolved $d^9$-bupivacaine into a 100 ml volumetric flask. The solution was diluted to 100 ml using a deionized water/MeOH (4:1) solution. Using successive dilutions, a series of samples of known concentrations were made as described in Table VII.

TABLE VII $d^9$-Bupivacaine Stock Solutions for Use as Internal Standard

| Stock Solution | Concentration | Volume Used | Diluted Volume | New Stock Solution |
|---|---|---|---|---|
|  | 10 mg |  | 100 ml | Bupd$^9$-1 (100 µg/ml) |
| Bupd$^9$-1 | 100 µg/ml | 0.5 ml | 50 ml | Bupd$^9$-2 (1 µg/ml) |

Bupivacaine was purchased from Sigma®. The bupivacaine stock solution was prepared by dissolving 20 mg of sample in about 5–10 ml MeOH in a vial, and then transferring the dissolved $d^9$-bupivacaine into a 200 ml volumetric flask. The solution was diluted to 200 ml using a deionized water/MeOH (4:1) solution. Using successive dilutions, a series of samples of known concentrations were made as described in Table VIII.

TABLE VIII

Bupivacaine Stock Solutions for Plasma Standards

| Stock Solution | Concentration | Volume Used | Diluted Volume | New Stock Solution |
|---|---|---|---|---|
|  | 20 mg |  | 200 ml | Bup-1 (100 µg/ml) |
| Bup-1 | 100 µg/ml | 5 ml | 50 ml | Bup-2 (10 µg/ml) |
| Bup-2 | 10 µg/ml | 5 ml | 50 ml | Bup-3 (1 µg/ml) |
| Bup-3 | 1 µg/ml | 5 ml | 50 ml | Bup-4 (100 ng/ml) |

A plasma sample (0.7 ml) was allowed to warm to room temperature (~25° C.). The sample was mixed, placed on a centrifuge for 20 min at 3200 rpm, and cooled to 5° C. 500 µl of the plasma sample was placed into a 12×75 mm test tube and the plasma samples were spiked with a known target compound (see table IX) in a blank plasma sample which was previously screened to determine that no interfering peaks were present. The plasma sample was mixed and 700 µl of the sample was placed in a 96-well collection plate. The sample was extracted using a solid phase extraction apparatus.

The solid phase extraction was performed on 3M Empore™ High Performance Extraction Disk plates (C18) with standard density 96-well as follows. The sorbent in each well was conditioned sequentially with 200 µl acetonitrile, 100 µl of MeOH, and then 200 µl of deionized water. The sample (700 µl) was loaded and a vacuum was applied until the sample was placed onto the sorbent. The absorbed sample was washed sequentially with 400 µl of deionized water and 400 µl of 10% MeOH in deionized water and a vacuum was applied. The sample was twice eluted with 200 µl of acetonitrile and twice reduced in volume under vacuum. The acetonitrile elutions were combined and the acetonitrile was removed by evaporation under a nitrogen gas flow at 40° C. for 30 min. The sample was reconstituted with 100 µl of H$_2$O/MeOH (4:1), and injected (35 µl) into the LC/MS system.

Using successive dilutions, a series of samples of the target compounds with known concentrations were made as described in Table IX.

TABLE IX

Plasma Standard Concentrations

| Standard Sample | Concentration of Dexamethasone | Concentration of Bupivacaine |
|---|---|---|
| STD 1 | 0.05 ng/ml | 5 ng/ml |
| STD 2 | 0.1 ng/ml | 10 ng/ml |
| STD 3 | 0.25 ng/ml | 25 ng/ml |
| STD 4 | 0.5 ng/ml | 50 ng/ml |
| STD 5 | 1 ng/ml | 100 ng/ml |
| STD 6 | 2 ng/ml | 150 ng/ml |
| STD 7 | 3 ng/ml | 200 ng/ml |
| STD 8 | 5 ng/ml | 300 ng/ml |

6.2.1.1 Materials and Apparatus

Dexamethasone and bupivacaine were purchased from Sigma® (St. Louis, Mo.). The 3M Empore® High Performance Extraction Disk plates (C18) with standard density 96-well were manufactured by 3M Filtration Products (St. Paul, Minn.). HPLC grade methanol and acetonitrile and reagent grade ammonium acetate were purchased from either Burdick & Jackson (Muskegon, Mich.) or Mallinckrodt Laboratory Chemicals, a Division of Mallinckrodt Baker, Inc. (Phillipsburg, N.J.). Deionized water having a conductivity of 18.2 MΩ was obtained from a Miller Q Plus™ water system manufactured by Miller Poll Corp.

Solutions of $NH_4OH$, $NH_4OH/MeOH$ were prepared as follows. Ammonium acetate (0.154 g, 2 mmol) was dissolved and mixed in 1000 ml of deionized water to obtain a 2 mM solution of $NH_4OAc$. A MeOH:$NH_4OAc$ solution was prepared by mixing 600 ml of MeOH into 400 ml of 2 mM $NH_4OAc$ to obtain a 3:2 MeOH:$NH_4OAc$ solution. Ammonium acetate (0.616 g, 8 mmol) was dissolved in 1000 ml of deionized water to obtain a 8 mM solution of $NH_4OAc$.

Internal standard solutions were prepared as follows. Flumethasone (10 mg, 0.02 mmol) was dissolved in 5 ml of MeOH and diluted to 100 ml with deionized water/MeOH 4:1 solution. This solution was labeled FluA at a concentration of 100 µg/ml. The FluA solution (0.5 ml) was diluted to a volume of 50 ml with a deionized water/MeOH 4:1 solution to obtain a solution labeled FluB at a concentration of ml. $d^9$-Bupivacaine (10 mg, 0.03 mmol) was dissolved in 5 ml of MeOH and diluted to 100 ml with a deionized water/MeOH 4:1 solution. This solution was labeled BvdA at a concentration of 100 µg/ml. The BvdA solution (0.5 ml) was diluted to a volume of 50 ml with a deionized water/MeOH 4:1 solution to obtain a solution labeled BvdB at a concentration of 1 µg/ml.

The mass spectrometer was a Micromass, Quatro LC LC/MS/MS system manufactured by Micromass LTD (Manchester, United Kingdom). The data was analyzed using Masslyn version 3.3 software. The liquid chromatograph is a Waters Alliance HT Separation Module 2790 manufactured by Waters Corp. (Milford, Mass.).

6.2.2 Results

The concentration of the known compounds versus the ratio of peak height of the sample/internal standard were plotted to obtain the calibration curves. FIG. 1 contains the plot of dexamethasone v. peak area ratio dexamethasone/internal standard. FIG. 2 illustrates the plot of bupivacaine v. peak area ratio bupivacaine/internal standard.

What is claimed is:

1. A method of detecting a corticosteroid and bupivacaine in a sample comprising:

a) adding internal standards for the corticosteroid and the bupivacaine to a sample comprising bupivacaine;

b) placing the sample on an HPLC column equilibrated with an acetate salt:MeOH solution and collecting an eluent; and c) analyzing the eluent of the HPLC column with a MS, wherein if the sample of step (a) comprises a corticosteroid, the corticosteroid and the acetate salt form a corticosteroid-acetate adduct, and bupivacaine and the adduct are detected by the MS.

2. The method according to claims 1, further comprising removing interfering compounds from the sample prior to step b).

3. The method according to claim 1 further comprising quantifying the amount of corticosteroid and/or bupivacaine wherein the peak height of the corticosteroid or bupivacaine is quantified using a calibration curve, said calibration curve is obtained by plotting data points of known concentrations of corticosteroid or bupivacaine versus a peak height ratio of (a known amount of corticosteroid or bupivacaine)/(internal standard).

4. The method according to claim 1, wherein the corticosteroid is beclomethasone, dexamethasone, flumethasone, or mixtures thereof.

5. The method according to claim 1, wherein the corticosteroid is dexamethasone.

6. The method of claim 1, wherein the acetate salt:MeOH solution is a $NH_4OAc$:MeOH solution.

7. The method according to claim 3, wherein the internal standard is beclomethasone, flumethasone, or mixtures thereof.

8. The method according to claim 3, wherein the internal standard is $d^3$-bupivacaine, $d^9$-bupivacaine, pentylcaine, or mixtures thereof.

* * * * *

UNITED STATES PATENT AND TRADEMARK OFFICE
CERTIFICATE OF CORRECTION

PATENT NO.    : 6,541,263 B2  Page 1 of 1
DATED         : April 11, 2003
INVENTOR(S)   : Feng Gao It is certified that error appears in the above-identified patent and that said Letters Patent is hereby corrected as shown below:

<u>Column 18,</u>
Line 42, replace "costeroid" with -- corticosteroid --

Signed and Sealed this

Twenty-ninth Day of July, 2003

JAMES E. ROGAN
*Director of the United States Patent and Trademark Office*